(12) United States Patent
Park et al.

(10) Patent No.: US 9,370,669 B2
(45) Date of Patent: Jun. 21, 2016

(54) DISPLAY DEVICE

(71) Applicant: Samsung Display Co., Ltd., Yongin, Gyeonggi-Do (KR)

(72) Inventors: Won-Sang Park, Yongin (KR); Jong-In Baek, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 254 days.

(21) Appl. No.: 14/152,118

(22) Filed: Jan. 10, 2014

(65) Prior Publication Data

US 2014/0254139 A1    Sep. 11, 2014

(30) Foreign Application Priority Data

Mar. 5, 2013  (KR) .......................... 10-2013-0023361

(51) Int. Cl.
| | |
|---|---|
| *F21K 99/00* | (2010.01) |
| *A61N 5/06* | (2006.01) |
| *G09G 3/20* | (2006.01) |
| *G09G 3/34* | (2006.01) |

(52) U.S. Cl.
CPC ................ *A61N 5/0618* (2013.01); *G09G 3/20* (2013.01); *A61N 2005/0662* (2013.01); *G09G 3/342* (2013.01); *G09G 2354/00* (2013.01); *G09G 2380/08* (2013.01)

(58) Field of Classification Search
CPC ........ A61N 5/0618; G09G 3/20; G09G 3/342
See application file for complete search history.

(56) References Cited

U.S. PATENT DOCUMENTS

| | | | | |
|---|---|---|---|---|
| 2006/0152525 A1* | 7/2006 | Woog | ..................... | G09G 5/003 345/589 |
| 2010/0264850 A1* | 10/2010 | Yamamoto | ............... | G09G 5/14 315/312 |
| 2012/0069551 A1 | 3/2012 | Bues et al. | | |

FOREIGN PATENT DOCUMENTS

| | | |
|---|---|---|
| KR | 10-2010-0042261 A | 4/2010 |
| KR | 10-2011-0098845 A | 9/2011 |

* cited by examiner

*Primary Examiner* — David V Bruce
(74) *Attorney, Agent, or Firm* — Robert E. Bushnell, Esq.

(57) ABSTRACT

Embodiments provide a display device including a first pixel unit and a second pixel unit. The first pixel unit may be formed on a first display area of a substrate so as to display an image. The second pixel unit may be formed on a second display area at the outside of the first display area and emit light with a peak wavelength band of about 460 to about 470 nm.

15 Claims, 2 Drawing Sheets

DISPLAY DEVICE

CLAIM OF PRIORITY

This application claims priority under 35 U.S.C. §119 of Korean Patent Application No. 10-2013-0023361, filed on Mar. 5, 2013, in the Korean Intellectual Property Office, the entire content of which are incorporated herein by reference in their entirety.

BACKGROUND OF THE INVENTION

1. Field of the Invention

Embodiments of the present invention generally relate to a display device, and more particularly, to a display device for artificially controlling biorhythm.

2. Description of the Related Art

Recently, a technique for controlling biorhythm by artificially controlling light environment has been developed [Oliver Stefani et al. "Evaluation of Human Reactions on Displays with LED Backlight and a Technical Concept of a Circadian Effective Display" SID 2010 Digest 75.4 (2010)].

Specifically, a living body has a clock mechanism (circadian clock) in the body, and controls periodic phenomena of vital functions. The representative phenomena are rhythm of sleeping/awakening, change in body temperature or blood pressure, etc. These phenomena are controlled by biorhythm.

Particularly, it has been studied that a hormone called melatonin is involved in controlling the rhythm of sleeping/awakening, and it has been found that the rhythm is controlled by change in the amount of melatonin secreted. And the change in the amount of melatonin secreted depends on light environment.

That is, the amount of melatonin secreted increases in a dark environment, and thus the sedative property of melatonin is exhibited. On the contrary, the amount of melatonin secreted decreases in a bright environment, and thus the awakening property of melatonin is exhibited.

This has been already studied, and an illumination device or display device with a melatonin control effect, to which the technique is applied, has been released in the market.

SUMMARY OF THE INVENTION

Embodiments provide a display device having a melatonin control effect, which can improve productivity.

In an embodiment of the present invention, a display device may include a first pixel unit formed on a first display area of a substrate so as to display an image, and a second pixel unit formed on a second display area at the outside of the first display area. The second pixel unit emits light with a peak wavelength band of about 460 to about 470 nm.

First pixels of the first pixel unit and second pixels of the second pixel unit may be formed in the same layer on the substrate.

Each second pixel may include a narrow-band organic light emitting element (organic light emitting diode (OLED)) having a peak wavelength band of about 464 nm.

A cathode electrode of the narrow-band organic light emitting element may have a thickness of about 190 to about 210 nm.

The display device may further include a backlight unit having a first light source formed in the first display area and a second light source formed in the second display area.

The first and second pixel units may be independently driven.

The second pixel unit may be driven at a predetermined time or user's selection.

The display device may further include an awakening mode controller configured to control the driving of the second pixel unit; and a user interface configured to receive a user's command input.

The second pixel unit emitting light with a peak wavelength band of about 460 to about 470 nm may be provided outside the first pixel unit displaying an image, thereby obtaining a melatonin control effect.

Further, the first and second pixel units may be formed in the same layer in the display panel, and it may be unnecessary to provide a separate light source. Furthermore, the thickness of the display device may not be increased, thereby further improving productivity and competitiveness of products.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

In the drawing figures, dimensions may be exaggerated for clarity of illustration. It will be understood that when an element is referred to as being "between" two elements, it can be the only element between the two elements, or one or more intervening elements may also be present. Like reference numerals refer to like elements throughout.

Figure 1A:
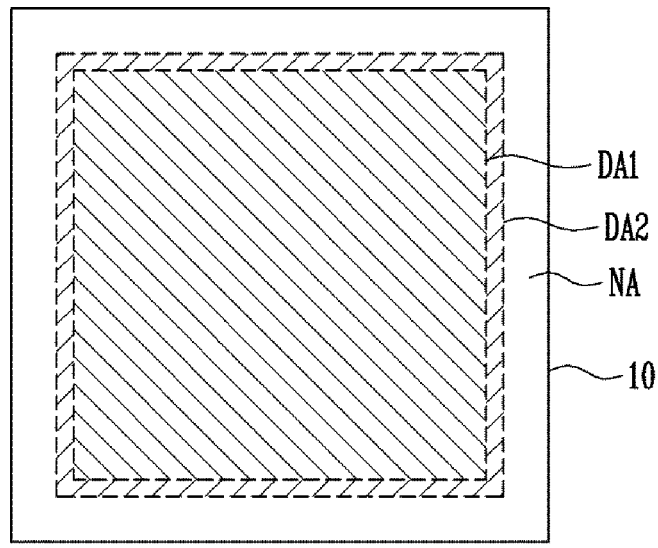
Figure 1B:
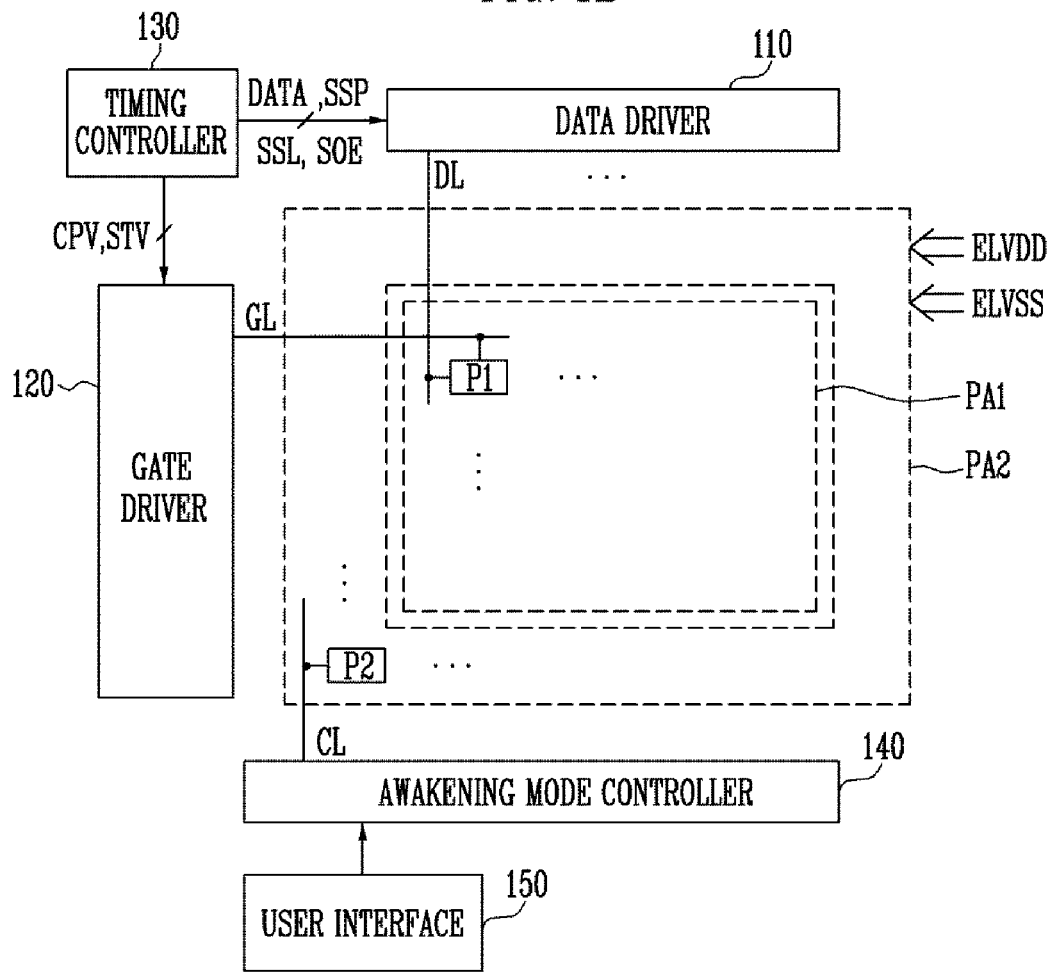
Figure 2:
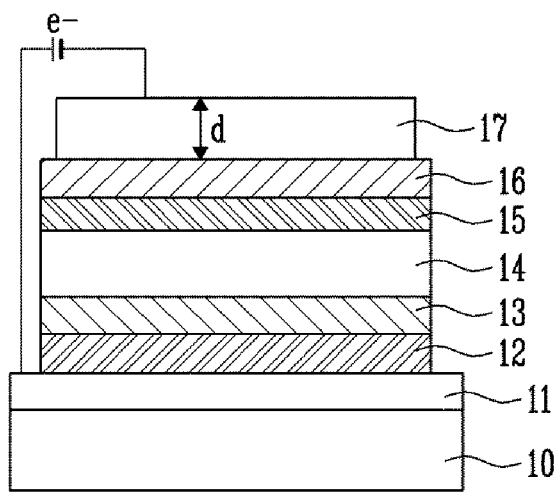

The above and other features and advantages of the present invention will become more apparent by describing in detail embodiments thereof with reference to the attached drawings in which:

FIG. 1A is a plan view illustrating a display device constructed as an embodiment according to the principles of the present invention;

FIG. 1B is a diagram schematically illustrating a configuration of the display device of FIG. 1A;

FIG. 2 is a sectional view illustrating a second pixel of FIG. 1B; and

Figure 3:
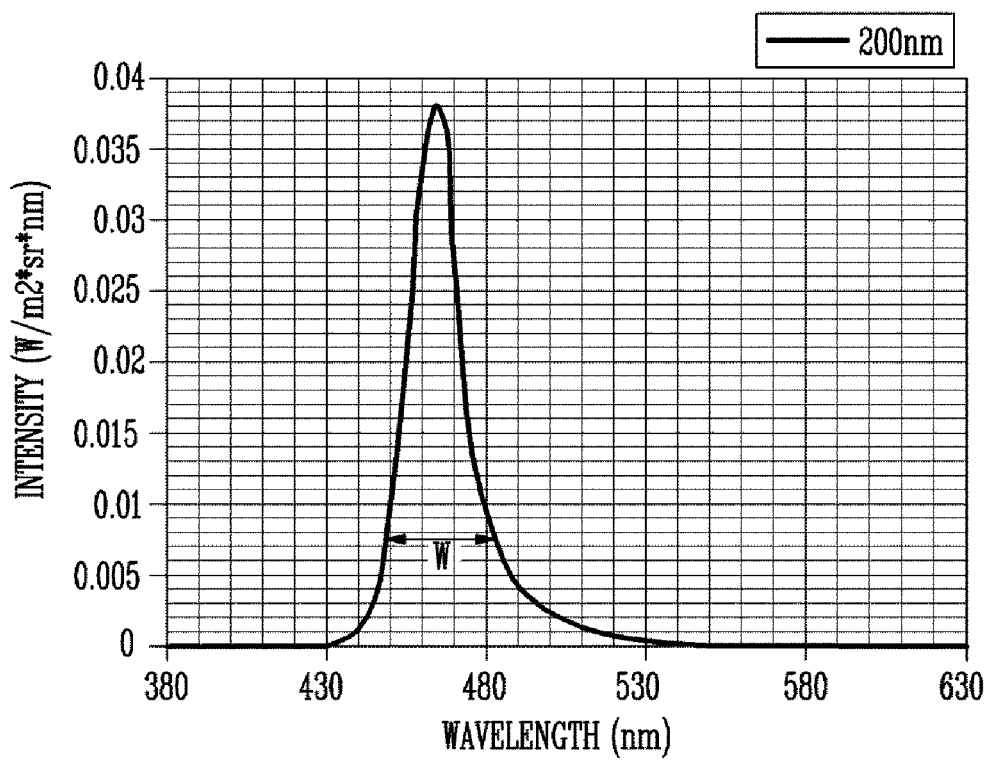

FIG. 3 is a graph illustrating a peak wavelength band of the second pixel of FIG. 2.

DETAILED DESCRIPTION OF THE INVENTION

Hereinafter, certain exemplary embodiments according to the present invention will be described with reference to the accompanying drawings. Here, when a first element is described as being coupled to a second element, the first element may be not only directly coupled to the second element but may also be indirectly coupled to the second element via a third element. Further, some of the elements that are not essential to the complete understanding of the invention are omitted for clarity. Also, like reference numerals refer to like elements throughout.

FIG. 1A is a plan view illustrating a display device constructed as an embodiment according to the principles of the present invention. FIG. 1B is a diagram schematically illustrating a configuration of the display device.

Referring to FIG. 1A, the display device according to this embodiment includes a substrate 10 divided into a first display area DA1 displaying an image, and a second display area DA2 and a non-display area NA, which are positioned at the outside of the first display area DA1.

Here, the second display area DA2 is an area which displays no image but emits light with a peak wavelength band of about 460 to about 470 nm.

The non-display area NA is an area which prevents visualization using a black matrix or the like. The non-display area NA performs a function of covering line patterns and driving circuits coupled to pixels in the first and second display areas DA1 and DA2.

The display device may be a liquid crystal display device, a field emission display device, a plasma display panel, an organic light emitting display device, etc. The substrate 10 may be an array substrate of the display device.

The display device may be integrally formed with a touch screen panel, and sensing electrodes (not shown) for sensing a touch input may be further formed on one surface of the substrate.

The substrate 10 may be made of a material having flexibility, transparency, heat resistance and chemical resistance. For example, the substrate 10 may be a thin film substrate made of one or more material selected from the group consisting of polyethylene terephthalate (PET), polycarbonate (PC), acryl, polymethyl methacrylate (PMMA), triacetyl cellulose (TAC), polyether sulfone (PES) and polyimide (PI).

Referring to FIG. 1B, the display device according to this embodiment may include a first pixel unit PA1, a second pixel unit PA2, a data driver 110, a gate driver 120, a timing controller 130, an awakening mode controller 140 and a user interface 150.

The first pixel unit PA1 is the first display area DA1 shown in FIG. 1A, and includes first pixels P1 positioned at intersection portions of gate lines GL and data lines DL.

The first pixels P1 are distributed at a predetermined interval in the first display area DA1, and may be arranged in a matrix form.

For convenience, one first pixel P1 has been illustrated in FIG. 1B, but the pixel shown in FIG. 1B is repetitively arranged in the first display area DA1.

Each first pixel P1 may include a light emitting element, and receives a high power voltage ELVDD and a low power voltage ELVSS, supplied from the outside of the display device. Here, the high power voltage ELVDD and the low power voltage ELVSS allow the light emitting element (organic light emitting diode (OLED)) to emit light.

Each first pixel P1 allows the light emitting element to emit light with luminance corresponding to a data voltage by supplying driving current or voltage to the light emitting element.

Each first pixel P1 controls the amount of current supplied to the light emitting element, corresponding to a data voltage transmitted through the data lines DL. The light emitting element emits light with luminance corresponding to the data voltage.

An embodiment of principles of the invention may be fabricated with each first pixel P1 may include a first subpixel which emits blue light, a second subpixel which emits green light, and a third subpixel which emits red light in response to the data voltage transmitted through the data lines DL. The peak wavelength band of the blue light emitted from the second display area DA2 may be within and narrower than a peak wavelength band of the blue light emitted from the first display area DA1.

The second pixel unit PA2 is the second display area DA2 shown in FIG. 1A, and includes second pixels P2 coupled to control lines CL.

In this embodiment, the second pixel unit PA2 has a shape surrounding the entire edge of the first pixel unit PA1. However, in another embodiment, the second pixel unit PA2 may be provided at one side or portion of the outside of the first pixel unit PA1.

The second pixels P2 are not coupled to the data lines DL and the gate lines GL but coupled to the control lines CL, so as to emit light under the control of the awakening mode controller 140.

Here, the first pixels P1 and the second pixels P2 may be formed in the same layer on the substrate 10.

That is, the first pixels P1 and the second pixels P2 are all arranged between upper and lower substrates of a display panel.

In some embodiments, the second pixels P2 may be formed using dummy pixels positioned at the outside of the first display area DA1.

The data driver 110 outputs, to each first pixel P1, a data voltage corresponding to an input image through the data lines DL.

The gate driver 120 outputs scan signals to each first pixel P1 through the gate lines GL.

In this case, the gate driver 120 may perform an operation of outputting an emission control signal to a plurality of emission control lines (not shown) coupled to the plurality of pixels.

The timing controller 130 generates and outputs control signals to the data driver 110 and the gate driver 120.

The timing controller 130 receives an input image signal and an input control signal for controlling display of the input image signal from an external graphic controller (not shown).

The timing controller 130 generates an input image data DATA, a source start pulse SSP, a source shift clock SSC, a source output enable SOE, etc. from the input image signal and the input control signal, and provides them to the data driver 110.

The timing controller 130 generates a gate driving clock CPV, a start pulse STV, etc., and outputs them to the gate driver 120.

The awakening mode controller 140 outputs a control signal to the second pixels P2 through the control lines CL.

The awakening mode controller 140 may control the on/off and brightness of the second pixels P2.

For example, if an awakening mode is activated, the awakening mode controller 140 outputs the control signal having a predetermined voltage so that the second pixels P2 can emit light.

In this case, the predetermined voltage may be a voltage applied to an anode electrode of an organic light emitting element (OLED) included in each second pixel P2. If the control signal is applied to the second pixel P2, the second pixel P2 can emit light with brightness corresponding to the potential difference between anode and cathode electrodes of the organic light emitting element.

Since different control signals are respectively input to the first and second pixel units PA1 and PA2, the first and second pixel units PA1 and PA2 may be independently driven.

The second pixel unit PA2 may be driven at a predetermined time or user's selection. To this end, the user interface 150 receiving a user's command input therethrough may be provided in the display device.

For example, the user may previously set the awakening mode to be automatically activated in a time zone when user's concentration is required, in consideration of a user's activity period or environment of the display device used. Alternatively, the user may turn on/off the awakening mode by pressing a predetermined button provided in the display device.

In the liquid crystal display device as another embodiment, light emitting elements are not arranged in a panel, and hence, the liquid crystal display device may include a backlight unit having a first light source formed in the first display area DA1 and a second light source formed in the second display area DA2.

Here, the second light source emits light with a peak wavelength band of about 460 to about 470 nm.

FIG. 2 is a sectional view illustrating the second pixel of FIG. 1B. FIG. 3 is a graph illustrating a peak wavelength band of the second pixel.

The second pixel P2 according to this embodiment may be implemented as a narrow-band organic light emitting element (OLED) having a peak wavelength band of about 464 nm. FIG. 2 illustrates a lamination structure of the organic light emitting element. FIG. 3 illustrates an intensity-wavelength graph of the organic light emitting element.

Referring to FIGS. 2 and 3, each second pixel P2 has a structure in which an anode electrode 11, a hole injection layer 12, a hole transport layer 13, an emission layer 14, an electron transport layer 15, an electron injection layer 16 and a cathode electrode 17 are sequentially laminated on a substrate 10.

Here, the thickness d of the cathode electrode 17 is formed within a range of 190 to 210 nm, so that the second pixel P2 can have a peak wavelength band of about 464 nm, which is further sharp, i.e., narrow in the width w of the wavelength band.

For example, the cathode electrode 17 may be made of a magnesium-silver alloy having a thickness "d" of about 200 nm. Thus, it is possible to implement a desired center wavelength and to improve resonance characteristics by changing the thickness and material of the cathode electrode 17 in the state in which the thicknesses and materials of the other layers except the cathode electrode 17 are the same as those in the first subpixels of the first pixels P1.

In order to emit light with a peak wavelength band of about 460 to 470 nm, the structure and material of the second pixel P2 may be variously modified.

The anode electrode 11 may be made of a transparent conductive material such as indium tin oxide (ITO). The anode electrode 11 may have a multi-layered structure together with metal such as aluminum.

The emission layer 14 determines a color of the organic light emitting element. In this case, the light with the peak wavelength band of about 460 to about 470 nm generally has a blue color.

The hole injection layer 12, the hole transport layer 13, the electron transport layer 15 and the electron injection layer 16 are laminated between the anode and cathode electrodes 11 and 17 so as to help the movement of electrons (or holes).

As described above, according to an embodiment of the present invention, the second pixel unit PA2 emitting light with a peak wavelength band of about 460 to about 470 nm is provided at the outside of the first pixel unit PA1 displaying an image, thereby obtaining a melatonin control effect.

Further, the first and second pixel units PA1 and PA2 are formed in the same layer in the display panel, and it is unnecessary to provide a separate light source. Furthermore, the thickness of the display device is not increased, thereby further improving productivity and competitiveness of products. Although not shown in the figures, the sequence of the layers that form the first pixel P1 and the second pixel P2 may be reversed. In this case, light emitted by the second pixel P2 transmits to an exterior of the display device via the anode electrode 11. In order to only allow the light with a peak wavelength band of about 460 to about 470 nm to be visible in the second display area DA2, the thickness and/or the material of the anode electrode 11 may be correspondingly changed according to the principles discussed above.

By way of summation and review, the illumination device or display device with a melatonin control effect that has been released in the market may use a separate light source for the purpose of providing the melatonin control effect.

For example, the product uses light with a wavelength of 464 nm that suppresses the secretion of melatonin. Therefore, a student or office worker using the product in the form of a lamp or computer monitor for a long period of time can concentrate on study or work in an awakening state.

However, in a related art display device, a separate light source is additionally provided for the purpose of the melatonin control effect. Therefore, manufacturing cost is increased, and the bezel width of a display panel is thickened.

According to an embodiment of the present invention, a display device may include: a first pixel unit formed on a first display area of a substrate so as to display an image; and a second pixel unit formed on a second display area at the outside of the first display area, and emitting light with a peak wavelength band of about 460 to about 470 nm.

According to an embodiment of the present invention, the second pixel unit PA2 emitting light with a peak wavelength band of about 460 to about 470 nm may be provided at the outside of the first pixel unit PA1 displaying an image, thereby obtaining a melatonin control effect.

Further, the first and second pixel units PA1 and PA2 may be formed in the same layer in the display panel, and it is unnecessary to provide a separate light source. Furthermore, the thickness of the display device is not increased, thereby further improving productivity and competitiveness of products.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A display device, comprising:
   a first pixel unit formed on a first display area of a substrate; and
   a second pixel unit formed on a second display area outside the first display area, and emitting light with a peak wavelength band of about 460 to about 470 nm, the first pixel unit including first pixels, the second pixel unit including second pixels, the first pixels being controlled by a first controller and the second pixels being controlled by a second controller.

2. The display device of claim 1, wherein the first pixels of the first pixel unit and the second pixels of the second pixel unit are in a same layer on the substrate.

3. The display device of claim 2, wherein each of the second pixels includes a narrow-band organic light emitting element having a peak wavelength band of about 464 nm.

4. The display device of claim 3, wherein an electrode of the narrow-band organic light emitting element, through which the light emitted by the narrow-band organic light emitting element is transmitted to an exterior of the display device, has a thickness of about 190 to about 210 nm.

5. The display device of claim 3, wherein an electrode of the narrow-band organic light emitting element, through which the light emitted by the narrow-band organic light emitting element is transmitted to an exterior of the display device, is made of a magnesium-silver alloy having a thickness of about 200 nm.

6. The display device of claim 1, further comprising a backlight unit having a first light source disposed in the first display area and a second light source disposed in the second display area.

7. The display device of claim 1, wherein the second pixel unit is driven at a predetermined time or user's choice.

8. The display device of claim 1, further comprising:
an awakening mode controller configured to control driving of the second pixel unit; and
a user interface configured to receive a user's command input.

9. A display device, comprising:
a plurality of first pixels formed on a first area of a substrate and displaying an image, each first pixel comprising a subpixel emitting a first light with a first peak wavelength band; and
a plurality of second pixels formed on a second area outside the first area, each second pixel emitting a second light with a second peak wavelength band, the second peak wavelength overlapping the first peak wavelength band and being narrower than the first peak wavelength band, the first pixels being controlled by a first controller and the second pixels being controlled by a second controller.

10. The display device of claim 9, wherein the first light is a blue light.

11. The display device of claim 9, wherein the second peak wavelength band is about 460 nm to about 470 nm.

12. The display device of claim 9, wherein
each subpixel of the first pixel comprises a first electrode, a second electrode, and a first light emitting layer interposed between the first electrode and the second electrode,
each second pixel comprises a third electrode, a fourth electrode, and a second light emitting layer interposed between the third electrode and the fourth electrode, and
a thickness of one of the first electrode and the second electrode, through which the first light is transmitted to an exterior of the display device, is different from a thickness of one of the third electrode and the fourth electrode, through which the second light is transmitted to the exterior of the display device.

13. The display device of claim 12, wherein one of the third electrode and fourth electrode, through which the second light is transmitted to the exterior of the display device, has a thickness of about 190 to about 210 nm.

14. The display device of claim 9, wherein
each subpixel of the first pixel comprises a first electrode, a second electrode, and a first light emitting layer interposed between the first electrode and the second electrode,
each second pixel comprises a third electrode, a fourth electrode, and a second light emitting layer interposed between the third electrode and the fourth electrode, and
a material forming one of the first electrode and the second electrode, through which the first light is transmitted to an exterior of the display device, is different from a material forming one of the third electrode and the fourth electrode, through which the second light transmits to the exterior of the display device.

15. The display device of claim 9, wherein the second pixels emit the second light for a predetermined interval of time in response to a command stored in the second controller or to a command received by the second controller via a user interface.

* * * * *